United States Patent
Bath

(10) Patent No.: US 6,544,254 B1
(45) Date of Patent: Apr. 8, 2003

(54) COMBINATION ULTRASOUND AND LASER METHOD AND APPARATUS FOR REMOVING CATARACT LENSES

(76) Inventor: Patricia Era Bath, 4554 Circleview Blvd, Los Angeles, CA (US) 90043-1146

( * ) Notice: Subject to any disclaimer, the term of this patent is extended or adjusted under 35 U.S.C. 154(b) by 17 days.

(21) Appl. No.: 09/604,892

(22) Filed: Jun. 28, 2000

Related U.S. Application Data

(60) Continuation-in-part of application No. 08/800,495, filed on Feb. 14, 1997, now Pat. No. 6,083,192, which is a continuation of application No. 08/474,773, filed on Jun. 7, 1995, now abandoned, which is a continuation-in-part of application No. 07/717,794, filed on Jun. 19, 1991, now abandoned, which is a continuation of application No. 07/159,931, filed on Feb. 24, 1988, now abandoned, which is a division of application No. 06/943,098, filed on Dec. 18, 1996, now Pat. No. 4,744,360.

(51) Int. Cl.⁷ .............................................. A61B 18/20
(52) U.S. Cl. ................... 606/6; 606/3; 606/10; 606/13; 604/22

(58) Field of Search .............................. 606/1, 2, 3–6, 606/10–17; 604/22, 20

(56) References Cited

U.S. PATENT DOCUMENTS 4,787,889 A * 11/1988 Steppe et al. ................. 604/22
6,083,192 A * 7/2000 Bath .............................. 606/1

FOREIGN PATENT DOCUMENTS

EP          189329   * 7/1986 .................. 606/46

* cited by examiner

Primary Examiner—David M. Shay

(57) ABSTRACT

The present invention is a method and apparatus for removing the lens of the eye in which pulsed ultrasound and laser energy are transmitted by means of an optical fiber delivery system to the lens of the eye for therapeutic purposes. The parameters of laser radiation are chosen to optimize the processes of photo-phacoablation and photo-phacodisruption. The vibrational frequencies of ultrasound are selected to optimize sono-fragmentation sono-cavitation. Both laser radiation and ultrasound energy are delivered in effective combinations to maximize the precise removal of cataractous lens material.

10 Claims, 2 Drawing Sheets

COMBINATION ULTRASOUND AND LASER METHOD AND APPARATUS FOR REMOVING CATARACT LENSES

This application is continuation in part application of application number 08/800,495 filed on Feb. 14, 1997, now U.S. Pat. No. 6,083,192, which is a Continuation of U.S. patent application No. 08/474,773, filed Jun. 7, 1995, now abandoned, which is a Continuation-In-Part of Application No. 07/717,794, filed Jun. 19, 1991, abandoned, which is a Continuation of Application No. 07/159,931, filed Feb. 24, 1988, now abandoned; which is a division of Application No. 06/943,098, filed on Dec. 18, 1986 which is now U.S. Pat. No. 4,744,360. Application Ser. No. 08/800,495 describes an ultrasound methodology for removing cataracts and U.S. Pat. No. 4,744,360 describes a laser device for removing cataracts. This continuation application describes a combined ultrasound and laser methodology for removing cataract lenses.

FIELD OF THE INVENTION

The present invention relates to a method and apparatus for coupling ultrasound and laser energy to an optical fiber combined with irrigation/aspiration for therapeutic purposes directed to and within a cataractous lens. With minor modification this invention can be adapted to treat other tissues within the human body.

BACKGROUND OF THE INVENTION

For many years optical fibers have been utilized in the medical industry to transmit light (laser energy) to targets for diagnostic as well as therapeutic purposes. Every eye is divided into an anterior and posterior chamber. When the lens becomes cloudy for any of a variety of reasons sight is impaired and the cloudy lens must be removed. This clouding of the lens is termed "cataract". Following removal of the lens, an intraocular lens (IOL) implant can be placed in the posterior chamber of the eye to replace the focusing function of the human lens. Alternatives to intraocular lens implants are thick spectacle eyeglasses or contact lenses to focus the light.

A number of techniques are now in use for this common surgical procedure. An incision, typically 3 mm can be made in the eye surface and a metal tipped ultrasonic probe is inserted to a position adjacent to the lens. The ultrasonic energy then fragments the lens material, which can then be removed by irrigation and aspiration.

Laser radiation is now widely used in various surgical techniques, particularly those involving the eye. For example, Krasnov U.S. Pat. No. 3,971,382 describes a technique in which laser radiation is focused onto the anterior capsule of the lens to form a hole through which the cataract substance can be drawn from the lens capsule.

Optical fibers are also commonly used for medical and other applications to transmit coherent radiation from a laser to some other location in the body where material is to be disintegrated or coagulated. U.S. Patent application Ser. No. 702,569 filed Feb. 19, 1985 describes a micro instrument with an optical fiber. The optical fiber can be inserted into the eye for removal of abnormal tissue such as tumors. Bath U.S. Pat. No. 4,744,360 describes a fiber-optic laser device for removing cataractous lenses. Coherent radiation with wavelengths between 193 nanometers and 3000 nanometers is said to be effective.

However, a problem with laser based systems is that there is the potential for explosions in the eye. Bath U.S. Pat. No. 4,744,360 teaches how to avoid explosions in the eye by first determining the ablation threshold and carefully configuring the laser parameters to deliver laser pulses to approximate the ablation threshold. Bath first determined the ablation threshold for human cataractous lenses to be approximately 0.5 $J/cm^2$ and published her results in Archives of Ophthalmology in 1987(volume 105, page 1164, 1987). The laser surgical parameters of energy density, power density, pulse duration, repetition rate and at a specific wavelength must be configured for optimal surgical effectiveness and safety. The teachings of Bath U.S. Pat. No. 4,744,360 and of the fundamentals of fiberoptic laser cataract surgery have spawned a plethora of devices and methods (referenced herein) for fiberoptic laser cataract surgery which is often referred to as laserphaco, i.e. laser phaco.

As above mentioned, it is known to use ultrasonic energy to disintegrate cataracts within the eye. This technique is known as phacoemulsification and was pioneered by Kelman. The phacoemulsification technique is limited because a metal tip associated with the technique becomes very hot at high frequencies, thereby potentially damaging the eye. Thus current practice has been to avoid performing the phacoemulsification procedure on "hard cataract nuclei" due to this heat problem, as well as the other technical difficulties associated with phacoemulsification.

The more dense cataract nucleus would require higher vibrational frequencies or increased phacoemulsification times thereby increasing the risk of heat related complications. Heat is produced at the target site of the vibratory motion, i.e. the cataractous lens, due, in part, to friction. This is a well known complication of ultrasonic processes and was recognized as early as 1967 as discussed by Delaney (vida infra, U.S. Pat. No. 3,352,303) who discusses "the problems associated with heat from wave (i.e. vibrational) energy . . . ."

The original and current phacoemulsification devices feature a metal cutting member which vibrates at high frequencies which is applied in direct contact with the cataractous lens.

This metal rod cutting member has been likened to a miniature "jack hammer". Significantly, in the art of reference related to ultrasound cataract surgery, the cutting member has always been fabricated of metal. The ultrasonic vibration of metal cutting members results in a finite percentage of heat related surgical complications such as "thermal wound injury".

In a special supplement to the Feb. 15, 1998 issue of Ocular Surgery News, there was an article written by Dr. Paul Ernest entitled "Thermal Wound Injury During Phacoemulsification" (pg.25–27). In this article, the occurrence of thermal wound injury was directly attributed to delays in irrigation and high phacoemulsification power settings. This publication is significant because the primary source of the "heat" problem, still goes unrecognized even in 1998. This reference also documents that the problem is also unsolved. The applicant's present invention addresses and solves this problem.

In summary, what is needed is a cataract removal system that does not have the heat problems associated with the phacoemulsification process and also is not susceptible to the explosions generated by laser based systems. The present invention addresses such a need. The present invention uses a non-metal optical fiber to delivery the combination of both laser energy and ultrasound energy to cataractous lenses in a safe and effective methodology.

SUMMARY OF THE INVENTION

The present invention relates to a method and apparatus in which pulsed ultrasound and laser energy are transmitted by means of an optical fiber delivery system to the lens of the eye for therapeutic purposes including cataract surgery. Combined laser and ultrasound energy are transmitted by a flexible line containing at least an optical fiber surrounded in part by an irrigation sleeve through a limbal incision on the eye surface, preferably 1 mm or less. A capsulotomy is made and the flexible line is advanced to a position immediately in contact with the crystalline lens. Ultrasound energy is delivered to the lens in pulsed doses. The vibrational frequencies are chosen based on the hardness of the lens nucleus in the specific surgical case. Vibrational frequencies are chosen to optimally cause processes of sonofragmentation, sonodisruption, sonocavitation of the lens nucleus. The placement of the irrigation sleeve to surround the fiberoptic results in cooling of the vibrational member. The circulation of irrigating fluid at and near the tip of the fiber also facilitates heat loss. Based on the knowledge of the ablation threshold for human lenses the parameters of the laser radiation are selected for transmission and delivery through the optical fiber. Laser parameters such as energy density, power density, pulse duration, repetition rate and wavelength are chosen to optimize processes of photophacoablation, photophaco-fragmentation, photophacodisruption, photophaco-decomposition. The propagation of ultrasound energy down a non-metal line for cataract surgery is novel in the art of cataract surgery. Another novel feature of Applicants' invention is the reduction of heat generated by ultrasonic vibratory mechanisms. This unexpected result is obtained because of the novel design and processes enabled by the continuous flow of irrigating fluids about the fiber optic. The use of a fiber-optic line for the dual transmission of ultrasound energy and laser energy for the purpose of fragmenting cataractous lenses is a second novel discovery demonstrated by applicant's invention.

The ultrasound and laser processes fragment the cataractous lens into extremely small particles less than 1 mm in diameter. These fragmented particles and lens cortex can be irrigated and aspirated from the capsular bag via an aspiration sleeve which is formed about and extending along the irrigation sleeve.

Since the particles produced by the laser and ultrasound processes are extremely small, the device can be made extremely small and therefore the surgical incision site can be made smaller. Smaller surgical incisions have the advantage of faster healing and more rapid visual rehabilitation. Utilizing an optical fiber further permits the energy to be more effectively and efficiently focused onto the lens to be removed.

The present invention employs an optical fiber which allows high frequency probe output without the high temperatures associated with conventional ultrasound probes for removing cataracts. In summary, the present invention exploits the advantage of utilizing an optical fiber to precisely deliver units of energy to loci within the lens. Moreover, the unique anatomy and biomechanical architecture of the lens lends itself to mechanical disruption resulting from photoacoustic and/or sonic processes.

DETAILED DESCRIPTION OF THE INVENTION

The present invention represents an improvement in the art of removing cataractous lenses because it combines the advantages of both ultrasound and cataract surgical methodologies. The following description is presented to enable one of ordinary skill in the art of cataract surgery to make and use the invention and is provided in the context of a patent application and its requirements. Various modifications to the preferred embodiment and the generic principles and features described herein will be readily apparent to those skilled in the art.

Applicant has observed that the optical fiber when conducting laser energy to the cataract lens vibrates. This phenomenon was described in Bath application Ser. No. 08/800495 in 1997. It was determined that some of the vibrations emanated from the lens itself as a result of laser-lens tissue interaction. At the instant of optical breakdown in the target zone, acoustic shock waves are created. These acoustic shock waves may be generated purposefully by configuration of laser parameters to maximize the photoacoustic component of each laser pulse. Short pulse durations in the nanosecond, picosecond or femtosecond range will minimize heat damage tissue effects and maximize non-linear mechanical photophysical effects as described by Boulnois in Lasers in Medical Science (volume 1, page 48, 1986, attached).

As demonstrated by Boulnois, one can configure the laser parameters to produce the desired predominant laser mechanism of photoablation, photodecomposition, photofragmentation, or photodisruption.

Figure 1:
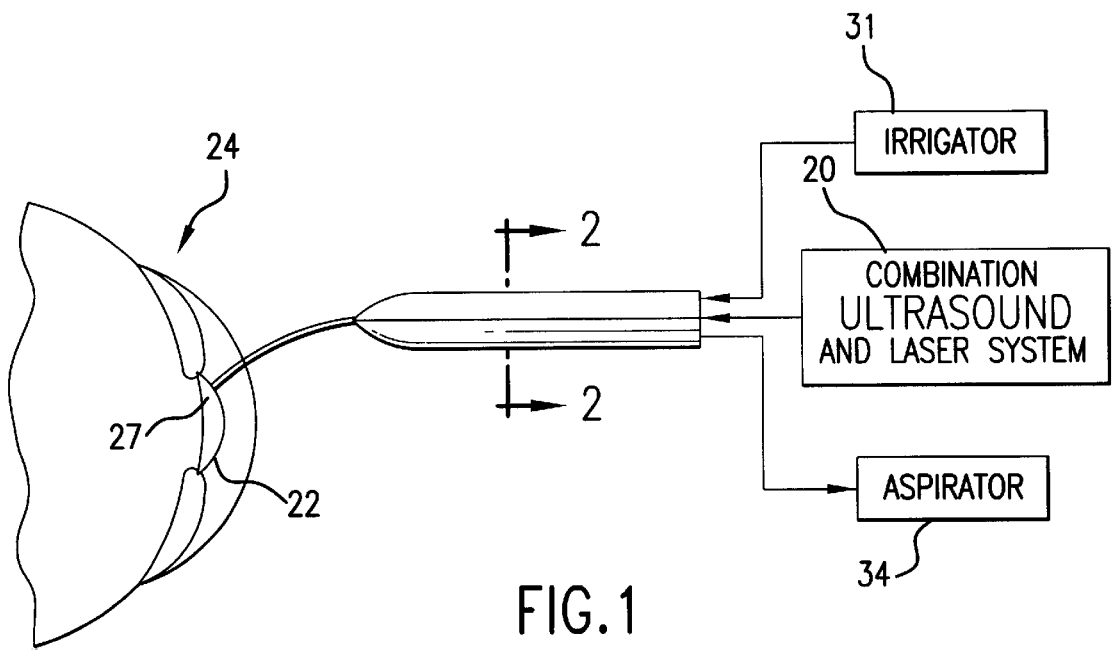
FIG. 1 shows a schematic view of the present invention being used for disintegrating a cataract lens. Note the distal endface (27) of the probe (26) in direct contact with the cataract lens.
Figure 1A:
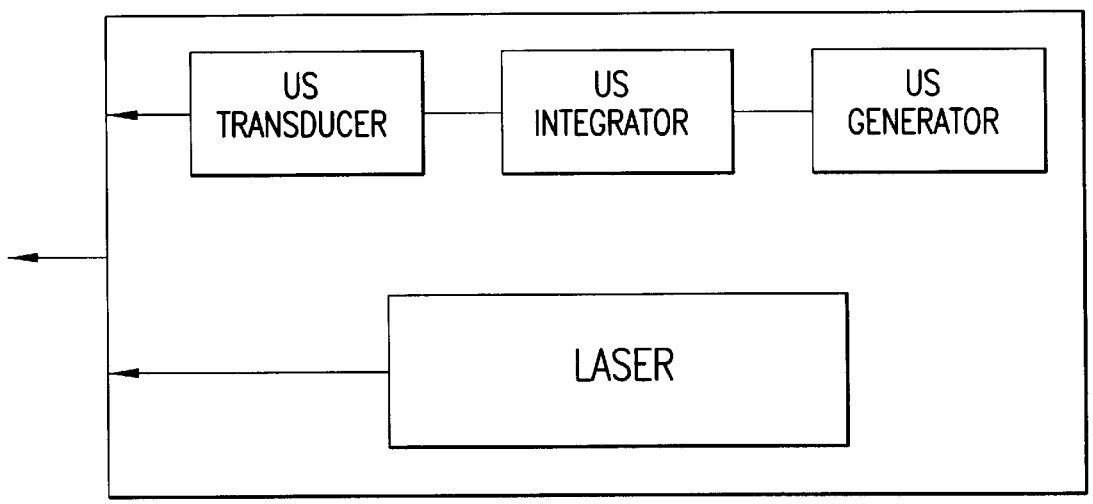
FIG. 1A is an exploded view of (20) and demonstrates the key features of the Ultrasound and Laser System.
Figure 2:
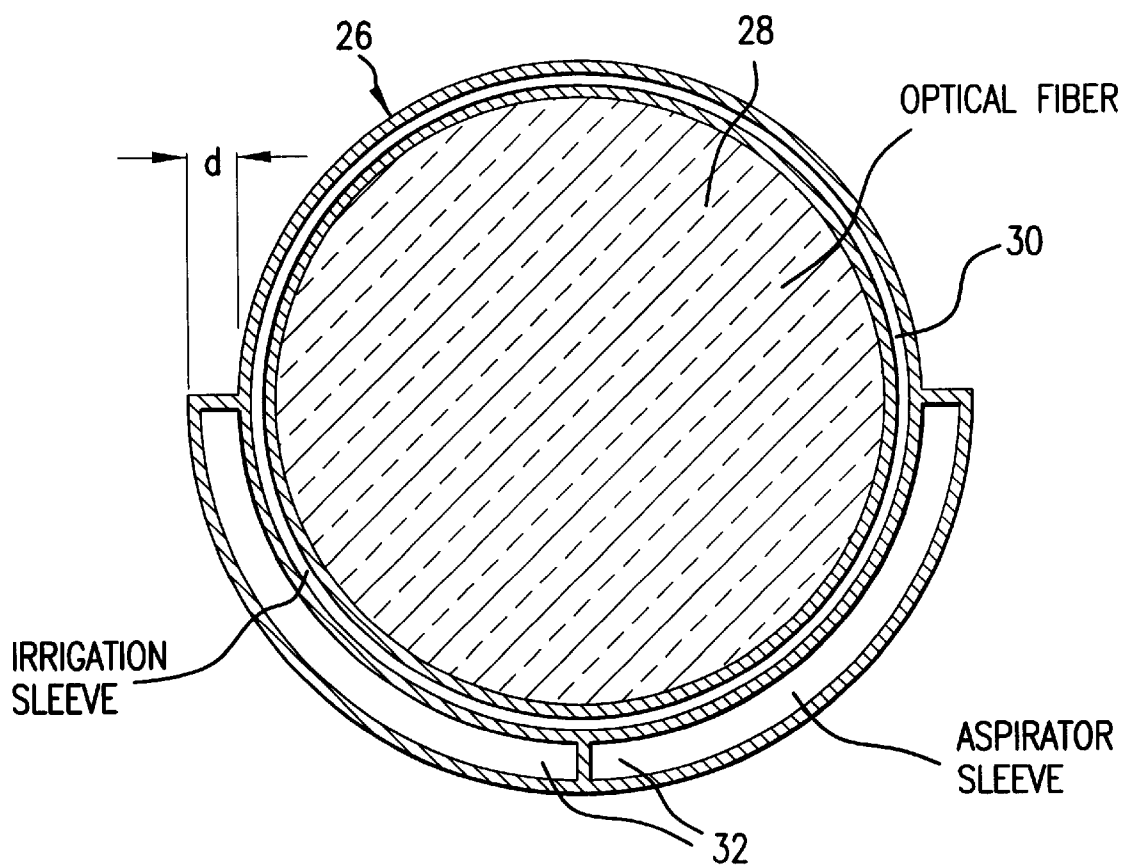
FIG. 2 shows a cross section of the flexible line of FIG. 1 along lines 2—2

Significantly, it was this observation of shock travelling along the optical fiber in the opposite direction of the laser energy that led to the hypothesis that shock waves could purposely be propagated down an optical fiber for therapeutic purposes. Heretofore, in the medical industry, the ability of optical fibers to transmit sound has only been exploited in the area of diagnostics. U.S. Pat. No. 5,217,018 dated June 1993 entitled "Acoustic Transmission Through Cladded Core Waveguide" for example, teaches such a use of an optical fiber. The above identified patent discloses: "This invention constitutes a major step forward in the continually evolving field of medical imaging". Accordingly, applicant has discovered that an optical fiber in combination with an ultrasound generator can be used for therapeutic purposes to fragment/emulsify cataractous lenses. In a preferred embodiment, the ultrasound generator includes a transducer located on a piezoelectric head to which a single strand optical fiber is linked. The preferred ultrasound generator will operate in a wide range of frequencies up to 100 MHz. The frequencies are generated at the proximal end of the optical fiber and the sound waves travel down the optical fiber and emerge in the vicinity of the distal endface (27) of flexible line 26. To more particularly describe the present invention, reference is now made to FIGS. 1, 1A, and 2 which illustrate a preferred embodiment of the present invention.

Typically, the cataractous lens is not homogeneous in its hardness or in its composition. For example, the central nuclear core is more dense than the peripheral nucleus. The percentage of water is definitively less in the central core lens nucleus than in the peripheral lens nucleus. Optically, the central core nucleus is more opaque than surrounding peripheral zones in the typical senile cataractous lens. These and other examples of non-uniformity formulate the scientific basis for varying the energy level and type of energy process for fragmentation at different localities with the human crystalline cataractous lens during the microsurgical procedure of cataract removal. The physical changes induced by ultrasound fragmentation are different from the physical changes induced by optical fragmentation by laser means.

Sonodisruption, sonocavitation, and sonofragmentation are biophysical mechanisms inherent to ultrasound effects on matter.

Therefore, based on the different physical, biomechanical, and biochemical zones of the cataract the applicant has invented a method that would optimize the fragmenting technique in proportion to the specific characteristics (biomechanical, biochemical) for each zone in each cataractous lens.

For example, the use of ultrasound is directly focused on the target zone of the cataractous lens to initiate the fragmentation process.

Macrofragments produced by the sonodisruptive process are then treated with pulsed coherent radiation, i.e., in the range of 193 nm to 3000 nm, to reduce the macrofragments into particles suitable for emulsification and aspiration.

Applicant's invention allows for surgeon modulation between laser and ultrasound modalities during the cataract surgery operation to optimize the removal process. For example, the processes of sono-phacodisruption and laserphaco-ablation are delivered in a synergistic methodology to optimize a safe and effective lens removal.

What is claimed is:

1. A method for removing cataractous lenses from an eye, comprising the steps of:
   transmitting laser radiation to a cataract,
   transmitting ultrasound energy to the cataract,
   observing the size of the particles generated by the transmission steps and
   adjusting the relative proportion of the laser and the ultrasound to optimize the size of the generated particles.

2. The method of claim 1, including the steps of:
   irrigating said generated particles with a fluid,
   aspirating said fluid entrained with particles from said cataractous lens.

3. A method for removing cataractous lenses from an eye, comprising the steps of:
   transmitting laser radiation to a cataract,
   transmitting ultrasound energy to the cataract,
   observing the size of the particles generated by the transmission steps and,
   adjusting the laser parameters of wavelength, power, and frequency to optimize the size of the particles generated by the transmission steps.

4. The method of claim 3 including the steps of:
   irrigating said generated particles with a fluid,
   aspirating said fluid entrained with particles from said cataractous lens.

5. A method for removing cataractous lenses from an eye, comprising the steps of:
   transmitting laser radiation to a cataract,
   transmitting ultrasound energy to the cataract,
   observing the size of the particles generated by the transmission steps and,
   adjusting the ultrasound parameters of amplitude, power, and frequency to optimize the size of the particles generated by the transmission steps.

6. The method of claim 5, including the steps of:
   irrigating said generated particles with a fluid,
   aspirating said fluid entrained with particles from said cataractous lens.

7. A method for removing cataractous lenses from an eye, comprising the steps of:
   transmitting laser radiation to a cataract,
   observing the size of the particles generated by the laser transmission step and,
   adjusting the laser parameters of wavelength, power, and frequency to optimize the size of the particles generated by the transmission step.

8. The method of claim 7 including the steps of:
   irrigating said generated particles with a fluid,
   aspirating said fluid entrained with particles from said cataractous lens.

9. A method for removing cataractous lenses from an eye, comprising the steps of:
   transmitting ultrasound energy to a cataract,
   observing the size of the particles generated by the transmission step and,
   adjusting the ultrasound parameters of amplitude, power, and frequency to optimize the size of the particles generated by the transmission step.

10. The method of claim 9, including the steps of:
    irrigating said generated particles with a fluid,
    aspirating said fluid entrained with particles from said cataractous lens.

* * * * *